United States Patent [19]

Fleisher

[11] Patent Number: 4,493,892

[45] Date of Patent: Jan. 15, 1985

[54] SOLVENT SYSTEM FOR PEROXIDASE INHIBITOR REAGENT FOR FECAL OCCULT BLOOD DETERMINATIONS

[75] Inventor: Martin Fleisher, Glen Cove, N.Y.

[73] Assignee: Memorial Hospital for Cancer & Allied Diseases, New York, N.Y.

[21] Appl. No.: 451,526

[22] Filed: Dec. 20, 1982

[51] Int. Cl.$^3$ ................... C12Q 1/28; G01N 33/72
[52] U.S. Cl. ........................... 435/28; 436/66
[58] Field of Search ............... 435/4, 28, 184; 436/66, 436/175

[56] References Cited

U.S. PATENT DOCUMENTS

| | | | |
|---|---|---|---|
| 3,996,006 | 12/1976 | Pagano | 422/50 |
| 4,017,261 | 4/1977 | Svoboda et al. | 435/28 |
| 4,175,923 | 11/1979 | Friend | 436/66 |
| 4,277,250 | 7/1981 | Melnick et al. | 435/28 |
| 4,333,734 | 6/1982 | Fleisher | 436/66 |

OTHER PUBLICATIONS

Dixon et al., *Enzymes*, Academic Press Inc., N.Y., p. 148, 1964.

*Primary Examiner*—Blondel Hazel
*Attorney, Agent, or Firm*—Felfe & Lynch

[57] ABSTRACT

A process and reagent for determining the presence of fecal occult blood in a test sample using a guaiac-peroxidase test matrix and a means for inhibiting peroxidase enzyme interferences which combines the partial denaturing of peroxidase enzyme protein using a protein-hydrogen bond cleaving agent, with the removal of metals necessary for efficient peroxidase enzyme activity wherein the improvement comprises dissolving said reagent for cleaving protein-hydrogen bonds in an alcohol-water solvent before adding said reagent to the sample.

13 Claims, No Drawings

SOLVENT SYSTEM FOR PEROXIDASE INHIBITOR REAGENT FOR FECAL OCCULT BLOOD DETERMINATIONS

BACKGROUND

This invention relates to a method of avoiding interferences which cause false-positive fecal occult blood determinations in stool samples when employing a method based on the reaction of guaiac with hemoglobin.

The avoidance of a false-positive test has, in the past, often relied on control of the dietary intake of the patient, when tests which rely on guaiac-peroxidase reagents are applied. An improved method of applying such tests is described in U.S. Pat. No. 4,333,734 by the same inventor hereof, wherein false-positive tests, due to the presence of peroxidase from ingested foods, are avoided. The basis of this method is a combination of the partial denaturing of peroxidase enzymes and the removal of necessary metals for efficient peroxidase enzyme activity. This combination of actions eliminates the interfering effect of peroxidase without requiring extreme conditions that might effect hemoglobin reactively.

During extensive clinical testing of the method and device of U.S. Pat. No. 4,333,734, it has been found that certain of the samples taken from patients still produce false-positive tests. It is believed that these false positive tests may be caused by drugs or drug metabolites, or a large variation in pH in the excrement of the patients.

The present invention has as its primary object the reduction or elimination of false-positive tests which occur due to interfering drug or drug metabolites when using the guaiac-peroxidase type reaction scheme for determination of hemoglobin in various samples.

BRIEF DESCRIPTION

Briefly, the present invention provides an aqueous alcohol solvent system which, due to solubility differences, retards the extraction of drugs from the sample into the reaction mixture, thereby practically eliminating the effect of drugs on the reactants when applying the guaiac-peroxidase test scheme. The inventive method is particularly useful in conjunction with, and is therefor an improvement over, the method described in U.S. Pat. No. 4,333,734. This prior method requires the application of an inhibitor reagent prior to the addition of the reaction initiator reagent, that is, a two step procedure. This leads to possible extraction of interfering drugs into the reaction zone by migration analogous to paper-chromatographic separations.

In the most preferred embodiment, the addition of mild acid to the reaction mixture enhances the rate of peroxidase inhibition and insures uniformity of reaction conditions. Color intensity for positive tests, is also enhanced.

DESCRIPTION OF THE PREFERRED EMBODIMENT

The present invention improvement for avoiding a false-positive test due to drug metabolites or other water soluble interfering substances is based on the use of solvent wherein the solubility of these substances is reduced, viz an alcohol containing solvent mixture. It has been found that a water-alcohol mixture, preferably about 50% alcohol to 50% water-depending on the alcohol used and the solubility of the various test system reagents in the resulting mixture-can be used to great advantage to improve the reliability of the prior art test procedure. Lower alcohols that are miscible over a wide range of compositions with water, such as methanol, ethanol, propanol, isopropanol and n-butanol, are useful in the practice of this invention. Of these, ethanol and isopropanol are preferred for their reasonable cost coupled with general availability and relative safety in handling.

The present invention also provides a method wherein the color intensity which results from applying the inventive test, is increased, by assuring that the reaction mixture remains slightly acid even in the presence of alkaline samples. This is accomplished by adding one or two drops of weak acid, especially acetic acid, to the sample smear on the slide. The acid also speeds up the rate of peroxidase inhibition when using the method of U.S. Pat. No. 4,333,734, from $2\frac{1}{2}$-3 hours normally encountered under non-acid conditions to 5-10 minutes with the acid addition and thereby provide a tremendous savings in time in running the procedure.

In the tables presented in this application, color intensity is scored as follows:

Negative—no color response
Trace—color response barely visible to naked eye
+1—slight color response
+2—moderate color response
+3—strong color response
+4—very strong color response Because higher alcohol to water ratios are expected to give the best results by minimizing interfering substance solubility, reagent solubility test were run to determine maximum alcohol concentration that can be used with the peroxidase denaturing reagents to be applied to the sample.

It was found that 6M guanidine hydrochloride and the EDTA reagent used for the inhibition of vegetable and fruit peroxidase activity in the known method, was not completely soluble in 70% aqueous solution of methanol, ethanol, isopropanol or n-butanol; The solubility of guanidine hydrochloride.EDTA in a 50% alcohol solution is effective except for n-butanol which showed solubility problem signs in the form of a fine suspension. Thus 50% aqueous alcohol was selected for the following experiment.

Following the procedure of Fleisher, U.S. Pat. No. 4,333,734 the reagents were modified to include a water-alcohol solvent, as follows:

Alcohol-inhibitor Solution

| | |
|---|---|
| 6M guanidine-hydrochloride | dissolved in 50% aqueous alcohol solution |
| 0.01 M EDTA | |

The effective concentration of this alcohol is about 35% because of the high specific volume of guanidine hydrochloride. Methanol, ethanol, isopropanol and n-butanol were tested.

Acid Reagent: 5M Acetic Acid
Experiments were run:
Prepared fecal occult test slides (guaiac impregnated) for detecting occult blood based on phenolic oxidation of guaiac by hemoglobin in the presence of hydrogen peroxide as a color developer (see U.S. Pat. No. 3,996,006), were used.

A 25 μl aliquot of horseradish peroxidase (0.36 mg/ml) was applied to each slide. Two drops of 5M acetic acid and 2 drops of alcohol inhibitor were added prior to addition of developer ($H_2O_2$). Developer was added at the time intervals indicated in the table below.

| Addition of developer ($H_2O_2$) After treatment with Inhibitor (minutes) | Untreated No Inhibitor | Methanol | | Ethanol | | Isopropanol | | n-butanol | |
|---|---|---|---|---|---|---|---|---|---|
| | | No Acid | Acid | No Acid | Acid | No Acid | Acid | No Acid | Acid |
| 10 | +4 | +1 | trace | +1 | trace | +3 | trace | +1 | trace |
| 15 | +4 | +1 | trace | trace | neg. | +2 | trace | +1 | trace |
| 30 | +4 | trace | neg. | trace | neg. | trace | neg. | trace | neg. |
| 90 | +4 | neg. | neg. | neg. | neg. | neg. | neg. | neg. | neg. |

DISCUSSION

A number of advantages of the use of modified peroxidase inhibitor reagent, according to the invention, have been observed and include the following:

1. The time for inhibition of peroxidase interferences is effectively reduced from about two-three hours to about 10 minutes. This can be seen from Table I (above), wherein only a trace of reaction is left after 10 minutes when acid is added to the reaction with modified reagent. Without the acid addition, the inhibition time is still only about 30 minutes to reduce the reaction to "trace".
2. Not only does the acetic acid help reduce the inhibition time, it also insures uniform test conditions for each sample. That is, the addition of mild acid such as acetic acid insures that the reaction mixture remains slightly acid even in the presence of alkaline samples.
3. The alcoholic matrix is more effective in testing patients exhibiting steatorrhea a condition in which the fat content of the stool is significantly increased. Prior treatment of the specimen with alcoholic inhibitor reagent reduces the hydrophobic consistency of the specimen and thus renders more effective the inhibition of peroxidase activity and reactivity of hemoglobin.
4. The color of positive guaiac reaction was found to be more vivid in positive tests. The latter may result from the uniformity of test acidity reducing the otherwise relatively rapid fading of color exhibited under positive test condition (i.e. presence of hemoglobin).

It will be understood that the specification and examples are illustrative but not limitative of the present invention and that other embodiments within the spirit and scope of the invention will suggest themselves to those skilled in the art.

What is claimed is:

1. In a process for determining the presence of fecal occult blood in a test sample which comprises inhibiting peroxidase enzyme interferences by partially denaturing the peroxidase enzyme protein using a protein-hydrogen bond cleaving agent, and simultaneously removing metals necessary for efficient peroxidase enzyme activity, and thereafter using a guaiac-peroxidase test matrix to determine fecal occult blood;
   the improvement comprising
      dissolving said protein-hydrogen bond cleaving agent in an alcohol-water solvent formed of approximately 20 to 50% by volume of methanol, ethanol, isopropanol or n-butanol in water; and thereafter adding said agent to the sample.
2. The process of claim 1 further comprising the step of adding weak acid having an acid strength approximately the same as acetic acid, to the reaction mixture before developing the color.
3. The process of claim 2 wherein the acid is acetic acid.
4. The process of claim 2 wherein 2 drops of acid are added to the sample.
5. The process of claim 1 wherein said reagent is guanidine, urea, or salicylic acid.
6. The process of claim 1 wherein said alcohol-water solvent comprises about equal volumes of water and alcohol.
7. The process of claim 6 wherein the reagent solution comprises 6M guanidine hydrochloride.
8. In a process for determining the presence of fecal occult blood in a test sample which comprises inhibiting peroxidase enzyme interferences by partially denaturing the peroxidase enzyme protein using protein-hydrogen bond cleaving agent, and simultaneously removing metals necessary for efficient peroxidase enzyme activity, and thereafter using a guaiac-peroxidase test matrix to determine fecal occult blood by the development of a blue color based on the phenolic oxidation of guaiac by hemoglobin in the presence of hydrogen peroxide,
   the improvement comprising
      adding a weak acid having an acid strength approximately the same as acetic acid to the reaction before developing the color.
9. The process of claim 8 wherein the mild acid is added before the reagent for cleaving protein hydrogen bonds is added.
10. The process of claim 8 wherein the acid is acetic acid.
11. The process of claim 10 wherein two drops of acid are added.
12. The process of claim 9 wherein two drops of acid are added.
13. A reagent for inhibiting peroxidase enzyme interference in the process for fecal occult blood determination of claim 1 comprising an effective amount of guanidine, urea or salicylic acid and EDTA dissolved in the alcohol-water solvent having a 20 to 50% by volume alcohol in water solution.

* * * * *